United States Patent [19]

Le

[11] Patent Number: 4,624,662
[45] Date of Patent: Nov. 25, 1986

[54] CATHETER FLUSHING SYSTEMS

[75] Inventor: Da H. Le, Pasadena, Calif.

[73] Assignee: Transamerica Delaval Inc., Lawrenceville, N.J.

[21] Appl. No.: 483,207

[22] Filed: Apr. 13, 1983

Related U.S. Application Data

[63] Continuation-in-part of Ser. No. 444,300, Nov. 24, 1982, abandoned.

[51] Int. Cl.$^4$ .................... A61M 5/00; F16K 51/00
[52] U.S. Cl. ............................ 604/249; 251/117; 251/320; 128/675
[58] Field of Search ............... 604/30, 33, 236, 246, 604/249; 128/675, DIG. 12; 251/DIG. 4, 217, 220, 320, 117, 322

[56] References Cited

U.S. PATENT DOCUMENTS

| | | |
|---|---|---|
| 1,983,227 | 12/1934 | Hall et al. |
| 2,181,900 | 12/1939 | Langdon |
| 2,524,474 | 10/1950 | Randel ........................... 251/322 X |
| 2,713,988 | 7/1955 | Kitterman ........................ 251/322 |
| 3,384,120 | 5/1968 | Bourget ......................... 251/321 X |
| 3,428,366 | 2/1969 | Harvey |
| 3,675,891 | 7/1972 | Reynolds et al. ................. 251/117 |
| 4,192,303 | 3/1980 | Young et al. .................... 251/117 |
| 4,278,083 | 7/1981 | Young et al. .................... 251/117 |
| 4,291,702 | 9/1981 | Cole et al. ..................... 128/675 |
| 4,300,571 | 11/1981 | Waldillig ....................... 604/30 X |
| 4,337,770 | 7/1982 | Young et al. .................... 604/30 |
| 4,341,224 | 7/1982 | Stevens ......................... 128/675 |

OTHER PUBLICATIONS

Graphic Controls, "Mid-Trace Pressure Monitoring Systems", p. 2.

Primary Examiner—Stephen C. Pellegrino
Attorney, Agent, or Firm—Benoit Law Corporation

[57] ABSTRACT

A catheter is flushed intermittently at a flushing flow rate higher than a seeping flow rate with the aid of a valve connected to a supply of flushing liquid. The valve has an operator of an elastic material providing an integral elastic sleeve about a valve stem, for biasing the operator to a rest position before and after manual actuation to a depressed position for a temporary opening of the valve. The operator is protected against accidental depression at all points thereof by a shield completely surrounding and surpassing the operator, so that a human finger has to penetrate into the shield for engagement of the operator prior to depression from its rest position against the bias of the elastic sleeve for an opening of the valve. The seeping flow rate is realized with a capillary passage which may extend along either a valve body or a valve seat in the valve and which is laterally bounded either by the valve seat or the valve body when the valve body is seated in the valve seat. The capillary passage is intermittently opened between continual flushings at the seeping flow rate and is then flushed at the higher flushing flow rate simultaneously with the catheter.

34 Claims, 9 Drawing Figures

CATHETER FLUSHING SYSTEMS

This is a continuation-in-part of my copending patent application Ser. No. 06/444,300, filed Nov. 24, 1982 now abandoned for Catheter Flushing Systems.

BACKGROUND OF THE INVENTION

1. Field of the Invention

The subject invention relates to hemodynamic pressure monitoring and similar systems, and to methods and apparatus for flushing catheters and similar devices at different flow rates.

2. Disclosure Statement

This disclosure statement is made pursuant to the duty of disclosure imposed by law and formulated in 37 CFR 1.56(a). No representation is hereby made that information thus disclosed in fact constitutes prior art, inasmuch as 37 CFR 1.56(a) relies on a materiality concept which depends on uncertain and inevitably subjective elements of substantial likelihood and reasonableness, and inasmuch as a growing attitude appears to require citation of material which might lead to a discovery of pertinent material though not necessarily being of itself pertinent. Also, the following comments contain conclusions and observations which have only been drawn or become apparent after conception of the subject invention or which contrast the subject invention or its merits against the background of developments subsequent in time or priority.

A main field of utility of the subject invention is apparent from the following patents dealing with catheter flushing apparatus and similar systems and being herewith incorporated by reference herein.

In particular, U.S. Pat. No. 3,675,891, by G. S. Reynolds et al, issued July 11, 1972, shows catheter flushing apparatus embodying a small block having therein passages for a flushing solution, with a flow resistor limiting the flushing to a small amount being located in one of the passages, and a valve being located in another passage connected by a bypass to the first passage for fast flushing upon manual pulling of a valve stem extending from a valve of resilient material through and beyond a wall of the flushing block. In practice, a certain safety factor thus gained tends to be encumbered by the disadvantage that typically both hands are required for actuation of the flushing valve. Moreover, it has been pointed out that the protruding stem of that device is subject to entanglement in tubing, bedding and the like, resulting in possible undesired opening of the valve or breakage of the valve stem so as to preclude proper operation of the device. It has also been pointed out that the valve stem can be broken by pulling the stem to one side or the other rather than longitudinally, and that the valve has been found occasionally to fail in the open position. Also, the presence in or at the liquid path of resilient material of which the valve body and a tubular extension thereof are made tends to introduce a dampening factor affecting a pressure sensing capability and quality frequently required in hemodynamic monitoring systems.

This problem is also present with the flow regulating devices for arterial catheter systems disclosed in U.S. Pat. No. 4,192,303, by J. E. Young et al, issued Mar. 11, 1980, and its continuation-in-part U.S. Pat. No. 4,278,083, issued July 14, 1981 and its division, U.S. Pat. No. 4,337,770, issued July 6, 1982, as well as with the continuous flushing apparatus disclosed in U.S. Pat. No. 4,245,636, by S. L. Sparks et al, issued Jan. 20, 1981. In particular, these flow regulating devices and flushing apparatus employ an outer flexible conduit which is squeezed for fast flushing in circumvention of a capillary passage. Moreover, those flow regulating devices and flushing apparatus appear exposed to the danger of unintended flushing through accidental depression of the outer flexible conduit, be it by a patient turning in bed or through another disturbing agency.

The latter problem may be somewhat alleviated in the first embodiment disclosed in U.S. Pat. No. 4,291,702, by J. E. Cole et al, issued Sept. 29, 1981 and in the corresponding embodiment of the related U.S. Pat. No. 4,341,224, by J. D. Stevens, issued July 27, 1982. In particular, those embodiments employ a design in which an actuator knob attached to an actuator shaft has to be pulled outwardly for the opening of a fast-flush valve. That design, however, again appears to require both hands for actuation of the valve. In an apparent effort to alleviate that problem, both of the latter patents propose second embodiments having a lever design for one-hand operation.

Unfortunately, such design appears, however, exposed to accidental actuation of the flushing valve. Moreover, the flushing apparatus of both of these patents require the presence of pressure pulse dampening elastomeric parts at the fluid path in the flushing apparatus.

The latter problem appears to be alleviated in a disposable flush device, sold by Graphic Controls, as Part No. 5100 and employing a helically coiled wire spring for biasing the flush valve to a closed position In that device, a capillary passage extends axially through the central valve body for flushing at a seeping flow rate when the valve is closed. Upon depression of an external fast flush button against the bias of the mentioned helical spring, the valve is opened and liquid can flush therethrough to the catheter, thereby bypassing the centrally disposed capillary passage which, of course, remains intact throughout the flushing operation, as well as before and thereafter.

The fast flush button in the latter device is disposed between two upwardly projecting portions of a lateral enclosure having a saddle-shaped circumference, whereby diametrically opposed portions of the fast flush button appear, nevertheless, to be exposed to accidental contact by fingers and objects and thereby to accidental actuation and consequent unintended release of the flushing operation.

Neither related nor different fields of endeavor appear to offer solutions for these problems. For instance, U.S. Pat. No. 3,298,367, by R. I. Bergman, issued Jan. 17, 1967, proposes apparatus for administering parenteral liquids employing capillary tubes connected in parallel between spaced headers. Conversely, U.S. Pat. No. 4,198,031, by F. D. Ezekiel et al, issued Apr. 15, 1980, proposes an automatic air deflation valve having an air flow channel extending longitudinally through a housing and a deformable diaphragm in an air deflection port extending outwardly from the channel and having a central aperture extending through the thickness thereof. The diaphragm deforms according to applied air pressure to automatically adjust the size and shape of the aperture, thus producing a constant air deflation rate therethrough.

U.S. Pat. No. 1,005,409, by H. T. Burns, issued Oct. 10, 1911, discloses a valve having a restricted passage for a continuous supply and a larger passage for a temporary increased supply with an internal spindle located in a threaded external spindle, both of which are subject to accidental actuation in practice. U.S. Pat. No. 1,983,227, by E. L. Hall et al, issued Dec. 4, 1934, discloses a gas pilot light control which is also vulnerable to accidental actuation.

On the other hand, the piston and flush valve disclosed in U.S. Pat. No. 2,181,900, by J. D. Langdon, issued Dec. 5, 1939, appears to require special tools for its adjustment and operation.

Further proposals appear to have one or more of the above mentioned disadvantages and to be of a generally too complex design for present purposes, as may be seen from U.S. Pat. No. 2,229,903, by L. H. Schmohl et al, issued Jan. 28, 1941, and disclosing a metering valve with several adjustable plugs, U.S. Pat. No. 2,411,667, by L. D. Mowrey, issued Nov. 26, 1946, and disclosing a bottom hole regulator including a valve mounted in a tubular body on a stem between a guide member and a valve seat, U.S. Pat. No. 2,655,170, by W. T. Ferguson, issued Oct. 13, 1953, and disclosing an air vent for water systems employing hydroscopic elements, U.S. Pat. No. 2,955,614, by R. E. Meynig, issued Oct. 11, 1960, for a constant tubing pressure choke for maintaining substantially constant fluid flow irrespective of variations in the pressure condition of a well pipe, U.S. Pat. No. 3,107,894, by F. R. Quinn, issued Oct. 22, 1963, for a snap action flow control valve with a Venturi formed between an orifice and a conical valve plug, U.S. Pat. No. 3,115,156, by F. R. Mortimer, issued Dec. 24, 1963, for a fluid pressure surge damper particularly for braking systems, U.S. Pat. No. 3,118,647, by W. H. Hasty, issued Jan. 21, 1964, for a valve assembly employing magnetic valve elements, U.S. Pat. No. 3,428,366, by C. H. Harvey, issued Feb. 18, 1969, for a flow control arrangement having a transverse channel for minimum operational flow in an actuable gate member, U.S. Pat. No. 3,474,816, by L. D. Burgess, issued Oct. 28, 1969, for purgeable gas pressure regulators, U.S. Pat. No. 3,877,428, by C. E. Seagle, issued Apr. 15, 1975 for a variable infusion control device providing a capillary flow path for administration of fluid parenterally at essentially uniform flow rates, and U.S. Pat. No. 4,173,296, by W. A. Marshall, issued Nov. 6, 1979, for apparatus for mixing and dispensing a beverage, including a mixing orifice system.

SUMMARY OF THE INVENTION

It is a general object of this invention to overcome the disadvantages and to meet the needs set forth in or apparent from the above disclosure statement, in any of the mentioned patents incorporated by reference herein, or in any other part hereof.

It is a germane object of this invention to provide solutions based on new approaches to the flushing, monitoring and operation of catheter systems.

It is a related object of this invention to provide improved flushing methods and apparatus.

It is also an object of this invention to increase the safety and reliability of operation of catheter and other flushing and monitoring systems and the well-being and safety of people relying thereon.

It is also an object of this invention to simplify design, construction and manufacture of catheter flushing and/or monitoring devices and of similar apparatus.

It is also an object of a particular aspect of this invention to dispense with the capillary tube heretofore consistently employed in catheter flushing devices for the purpose of providing a seeping flow rate.

Other aspects of this invention will become apparent in the further course of this disclosure.

From a first aspect thereof, the subject invention resides in a method of, or in apparatus for, flushing, or making a valve enabling flushing of a catheter intermittently at a flushing flow rate higher than a seeping flow rate with the aid of a valve connectable between a supply of flushing liquid and the catheter and having a valve stem and a manually actuable valve operator on an end portion of the valve stem and engageable by a human finger for depression from a rest position, in which the valve is closed to flushing at the flushing flow rate, to a depressed position in which the valve is open for flushing of the catheter at the flushing flow rate.

According to this first aspect thereof, the invention resides in the improvement comprising, in combination, the steps of, or means for, making the operator of an elastic material providing an integral elastic sleeve about the end portion of the valve stem, employing the integral elastic sleeve for biasing the operator to the rest position before and after manual actuation against the bias of the elastic sleeve to the depressed position, and protecting the operator against accidental depression at all points thereof by completely surrounding the operator with a shield surpassing the operator around its entire circumference so as to require the human finger to penetrate into the shield for engagement of the operator prior to depression from the rest position against the bias of the elastic sleeve for an opening of the valve.

From a second aspect thereof, the invention resides in the improvement comprising in combination, the steps of, or means for, providing the valve stem with a snap-on connector end at the operator, providing the operator with a retainer and providing the retainer with a snap-on connection means for retaining the operator at the valve stem via the snap-on connector end, and retaining the operator at the valve stem with the retainer connected via the snap-on connection means to the snap-on connector end.

From another aspect thereof, the subject invention resides in a method of or in apparatus for, flushing, or making a valve enabling flushing of a catheter continually at a seeping flow rate through a capillary passage and intermittently at a higher flushing flow rate upon an opening of said capillary passage.

According to this latter aspect, the subject invention resides more specifically in the improvement comprising, in combination, the steps of, or means for, providing a manually actuable operator for intermittently opening said capillary passage, and protecting the capillary passage against accidental opening by completely surrounding the operator with a shield surpassing the operator around its entire circumference.

From yet another aspect thereof, the invention resides in apparatus for flushing a catheter continually at a seeping flow rate through a capillary passage and intermittently at a higher flushing flow rate, and, more specifically, resides in the improvement comprising, in combination, a flushing liquid outlet on the apparatus connectable to the catheter, an outlet passage extending in that apparatus from the capillary passage to the outlet and means for sensing liquid pulsations in the outlet passage between the capillary passage and the outlet, including a built-in transducer integral with the apparatus and having a pressure sensitive component in the apparatus only near the liquid outlet opposite the capillary passage, for sensing liquid pulsations in the outlet passage in the apparatus.

From a related aspect thereof, the invention resides in a combination including a flushing liquid outlet on the apparatus connectable to the catheter, an outlet passage extending in the apparatus from the above mentioned capillary passage to the outlet and including a concave cavity increasing in diameter from a bottom region to a wider top opening facing the capillary passage, and means for sensing liquid pulsations in the outlet passage and the outlet, including a built-in transducer integral with the apparatus and having a pressure sensitive component at the bottom region of the concave cavity, for sensing liquid pulsations in the outlet passage.

BRIEF DESCRIPTION OF THE DRAWINGS

The subject invention and its various objects and aspects will become more readily apparent from the following detailed description of preferred embodiments thereof, illustrated by way of example in the accompanying drawings, in which like reference numerals designate like or functionally equivalent parts, and in which.

DESCRIPTION OF PREFERRED EMBODIMENTS

The catheter flushing devices 10 and 100 shown in the drawings have an inlet nipple, pipe or passage 12 carrying a conventional fitting 13 for attachment to a flushing fluid supply. Reference may in this respect be had to the above mentioned Reynolds et al, Young et al, Sparks et al, Cole et al, and Stevens patents incorporated by reference herein (hereinafter "incorporated patents") for a description of examples of utility for the flushing devices 10 and 100 and for a showing of systems in which they may be used. By way of example, the inlet passage 12 may, for instance, be connected via a diagrammatically illustrated line 14 to a fluid or flushing liquid supply 15 which, for instance, may be of a type shown in the first figure of each above mentioned Young et al patent or of a type otherwise described in the incorporated patents.

Each of the catheter flushing devices 10 and 100 also has an outlet nipple, pipe or passage 16 equipped with a Luer-type or other attachment fitting 17 for connection to a diagrammatically illustrated line 18 of a catheter system 19 which, for instance, may be of the type illustrated in the first figure of each of the above mentioned Young patents or of a type otherwise described in the incorporated patents.

Each of the catheter flushing devices 10 and 100 shown in FIGS. 1 to 6 also has a nipple, pipe or passage 21 having an attachment fitting 22 for connection via a diagrammatically illustrated line 23 to a pressure or other monitor 24 which, for instance, may be of the type shown in the first figure of the above mentioned Stevens patent or of a type otherwise disclosed or mentioned in the incorporated patents.

Each of the catheter flushing devices 10 and 100 incorporates methods and apparatus for flushing a catheter 19 intermittently at a flushing flow rate higher than a seeping flow rate with the aid of a valve 26 connected or connectable between a supply of flushing liquid 15 and the catheter 17 and having a valve stem 27 or 127 and a manually actuable button or valve operator 28 on top or on an end of the valve stem. The operator 28 or 128 is engageable by a human finger 29 shown only in FIG. 3 but equally applicable to the operator 128 of FIGS. 6 et seq.

Figure 1:
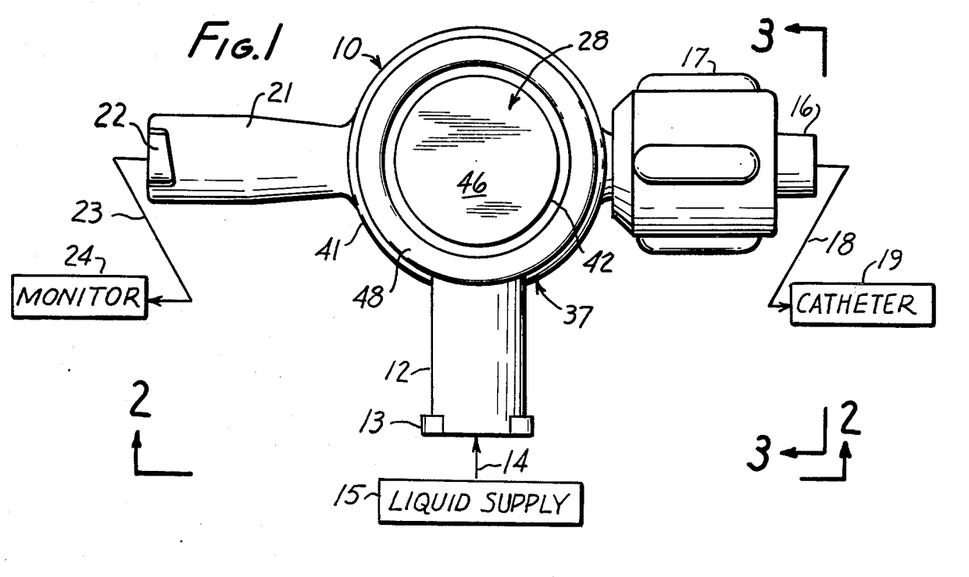
FIG. 1 is a top view of a catheter flushing device according to a preferred embodiment of the subject invention.
Figure 2:
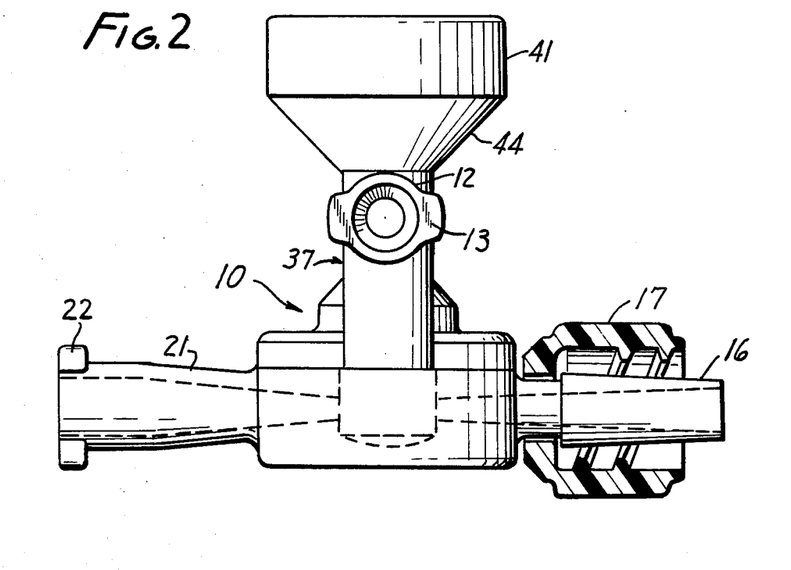
FIG. 2 is an elevation, partially in section, taken on the line 2—2 of FIG. 1.
Figure 3:
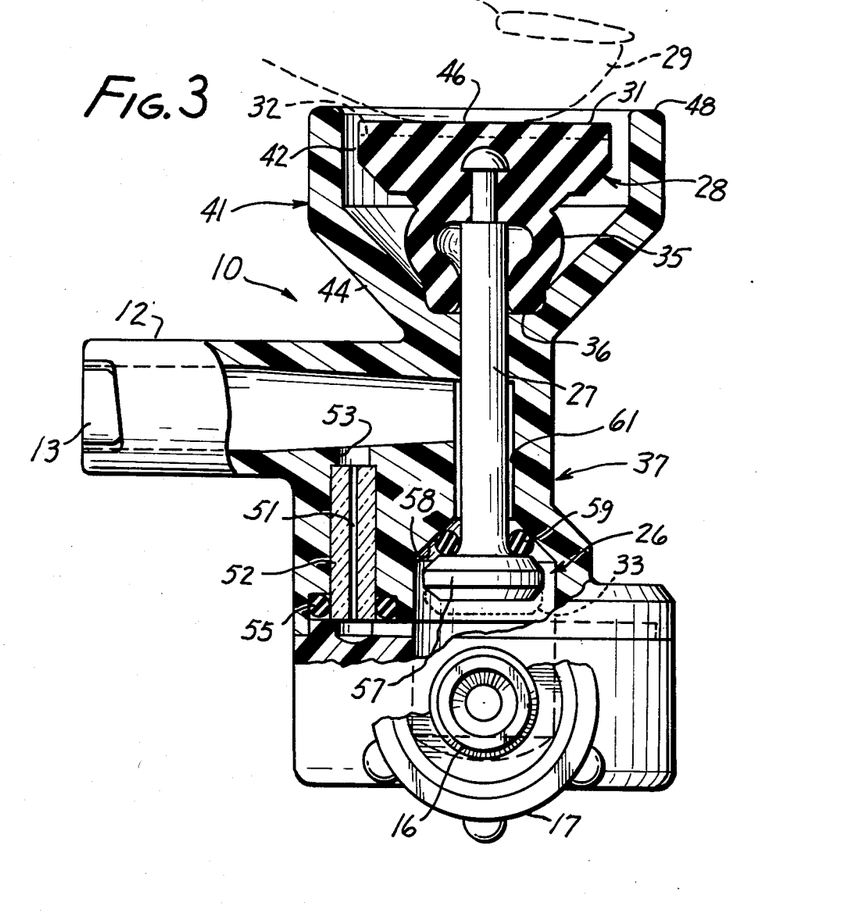
FIG. 3 is an elevation, partially in section, taken on the line 3—3 of FIG. 1.
Figure 5:
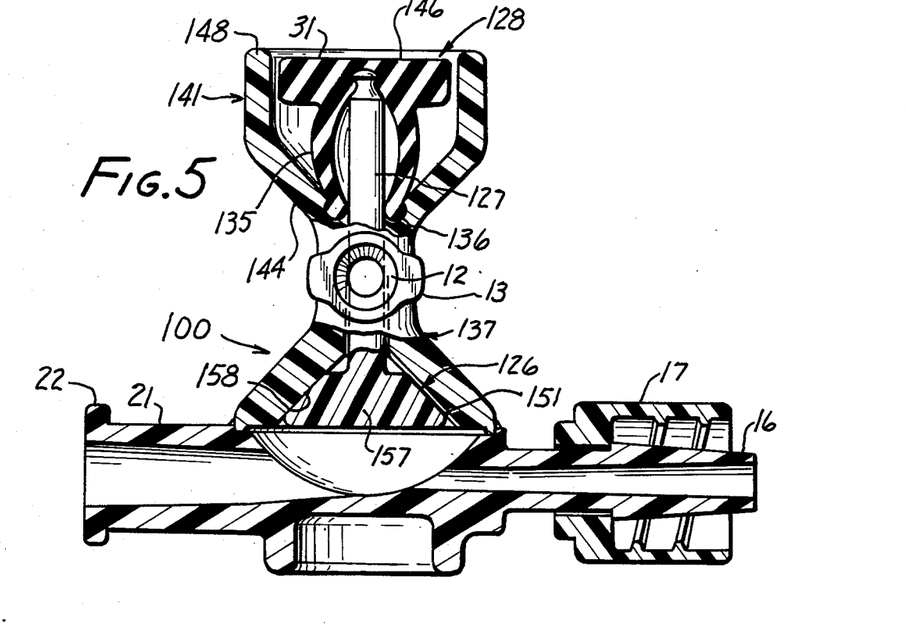
FIG. 5 is an elevation, partially in section, taken on the line 5—5 of FIG. 4.
Figures 6, 7:
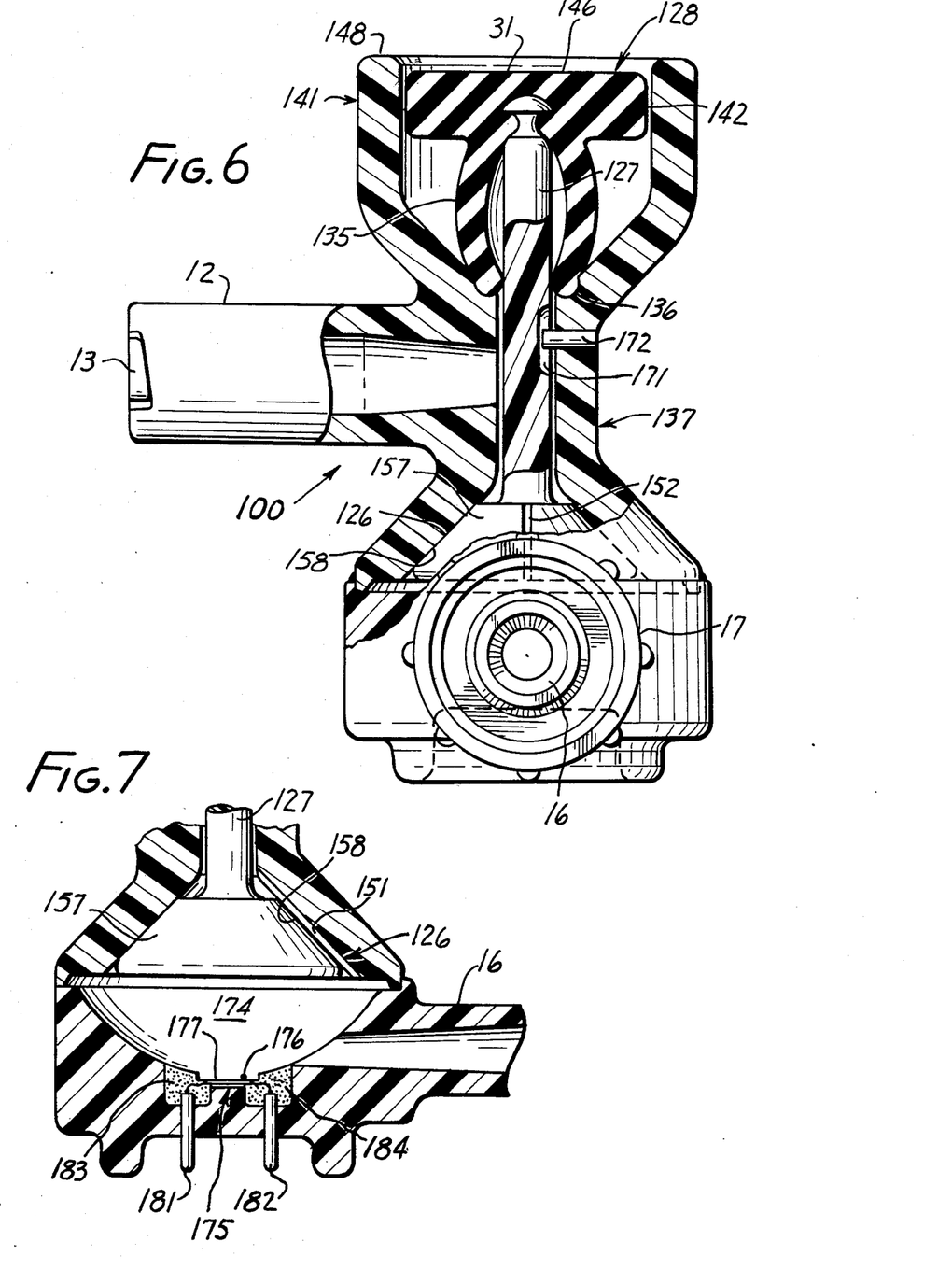
FIG. 6 is an elevation, partially in section, taken on the line 6—6 of FIG. 4.
FIG. 7 is a detailed view, in section, of a modification of the device shown in FIGS. 4 to 6, according to a further embodiment or aspect of the subject invention.

The operator 28 or 128 is thus engageable by the human finger 29 for depression from a rest position 31 shown in solid outlines in FIGS. 3, 5 and 6, in which the valve is closed to flushing at the flushing flow rate, to a depressed position 32 indicated by a dotted line in FIG. 3, in which the valve 26 or 126 is open as indicated in dotted outline at 33, for flushing of the catheter 19 at the higher flushing flow rate.

Each of the operators 28 and 128 is made of an elastic material providing an integral elastic sleeve 35 or 135 about the valve stem 27 or 127. Both embodiments thus employ the integral elastic sleeve 35 or 135 for biasing the operator 28 or 128 to the rest position 31 before and after manual actuation against the bias of such elastic sleeve to the depressed position 32. In other words, both illustrated preferred embodiments have means for biasing the operator to the rest position 31 before and after manual actuation, including an elastic sleeve 35 or 135 integral or of one piece with the operator 28 or 128 and extending about the valve stem 27 or 127 to a relatively stationary portion 36 or 136 of the flushing device 10 or 100 or of a housing 37 or 137 thereof.

In both illustrated embodiments, the operator 28 or 128 is protected against accidental depression at all points thereof by completely surrounding the operator with a shield 41 or 141 surpassing the operator around its entire circumference 42 or 142 so as to require the human finger 29 to penetrate into the shield 41 or 141 for engagement of the operator 28 or 128 prior to depression from the rest position 31 against the bias of the elastic sleeve 35 or 135 for an opening of the valve 26 or 126.

The shield or means for protecting the operator 28 or 128 against accidental depression may be formed of or as a part of the flushing device housing 37 or 137 and may be provided with a tapered or undercut portion 44 or 144 permitting engagement by further fingers (not shown) of the human hand with which the catheter flushing device 10 or 100 is operated. For instance, the housing 37 or 137 may be held between a person's index and middle finger engaging opposite sides of the tapered portion 44 or 144 while a thumb 29 engages the operator 28 or 128 through the top opening of the shield 41 or 141 and depresses such operator from its rest position 31 to its active position 32 at which the fast flushing valve 26 or 126 is opened.

For the required protective action, the operator 28 or 128 is provided with a top surface 46 or 146 engageable by the human finger 29 and being at all points and in all positions 31, 32, etc., inside the shield 41 or 141.

Similarly, the shield 41 or 141 is provided with a circular or otherwise endless rim 48 or 148 surpassing the operator 28 or 128 at all points and in all positions thereof.

The protective features thus implemented favorably distinguish the preferred embodiments of the subject invention from the projecting pull stems, exposed outer squeezable conduits, and fully or partially exposed actuator knobs, buttons and levers, all of which could be and frequently were accidentally engaged with a resulting accidental flushing of the catheter system and organisms connected thereto.

As for instance shown in FIG. 3, a capillary passage 51 bypassing the valve 26 is provided as a means for flushing the catheter 29 at the seeping flow rate. By way of example, the capillary passage may extend axially through a rod 52 of glass mounted in a bypass 53 extending between the inlet passage 12 and outlet passage 16 in parallel to the valve 26. An O-ring 55 shown in FIG. 3 surrounds the capillary passage 51 or tube 52 to prevent undesired seepage in the bypass 53 along the outside of the tube 52.

In the trade, tubes of the type shown at 52 in FIG. 3 are frequently referred to as "marine-bore" tubes having capillary passages in the micron or ten micron range affording a high resistance to the flow of infusion solution or other employed liquid as long as the valve 26 is closed. In this manner, an only seeping flow rate is established for continuous operation or, more precisely, continual operation between fast flushings.

According to the embodiment illustrated in FIG. 3, the valve 26 has a valve body or plunger 57 connected to or integral with the valve stem 27, and a corresponding valve seat 58. The plunger 57 carries an O-ring 59 which is squeezed between the plunger and the valve seat 58 when the valve 26 is closed by the bias of the flexible sleeve 35 and the operator 28 then resting in its top position 31 inside of and below the endless rim 48 of the protective shield 41.

When the operator 28 is engaged by a human finger 29 through the surmounting shield 41 and is depressed to its actuated position 32, the valve 26 is opened by a removal of the O-ring 59 from the valve seat 58 upon a downward movement of the valve plunger 57 indicated by a dotted outline 33. Accordingly, flushing liquid or other solution continuously applied to the inlet passage 12 can proceed at the higher flushing flow rate through the passage 61 past the valve stem 27 and inbetween the valve seat 58 and removed O-ring 59 to the outlet passage 16 of the catheter flushing device 10. Since the effective cross-section of the thus opened valve passage 61 is many times larger than the tiny cross-section of the capillary passage 51, the catheter is thus flushed at the flushing flow rate higher than the seeping flow rate whenever the operator 28 is depressed and the valve 26 opened.

The valve 126 as seen in FIGS. 5 to 7 has a conical valve body 157 connected to the valve stem 127 and a frustoconical valve seat 158 for seating the valve body 157.

The elastic sleeve 135, resting against the housing portion 136, biases the valve stem 127 and operator 128 upwardly to the resting position 31 inside the shield 141, thereby pressing the valve body 157 into tight engagement with the valve seat 158. Accordingly, the valve 126 is closed and prevents flushing of the catheter 19 at the higher flow rate. However, the second illustrated preferred embodiment, like the first embodiment, continuously or continually flushes the catheter at the seeping flow rate through a capillary passage during the intervals between depression of the operator 128 and openings of the valve 126. In other words, the second preferred embodiment includes means for flushing the catheter 19 at the seeping flow rate when the valve body 158 is seated in its valve seat 158. As shown in FIGS. 5 and 7, the capillary passage 151 in the second preferred embodiment of the subject invention extends between and along the valve body 157 and the valve seat 158 for flushing of the catheter at only the low seeping flow rate as long as the valve 126 is closed to flushing at a higher rate, and for alternatively flushing the catheter 19 at a rate higher than the seeping flow rate upon depression of the operator 128 and opening of the valve 126. In other words, in it solidly illustrated position shown in FIGS. 5 to 7, the valve 126 is closed to all but a seeping flow through the capillary passage 151.

As shown in FIGS. 5 and 6, the capillary passage 151 may be provided in the form of a groove along the valve seat, in effect bypassing the valve 126 or valve body 157.

Alternatively or additionally, as shown in FIG. 6, the or a capillary passage 152 may be provided in the form of a groove along the valve body 157, in effect bypassing the valve 126 or valve seat 158 for a seeping flow rate while the valve is in its otherwise closed condition.

The capillary passage 151 or 152 thus include a groove in a surface of at least one of the valve body 157 and valve seat 158, with that capillary passage 151 or 152 extending along and being laterally bounded by the other of the valve body 157 and valve seat 158, when the valve body is seated in such valve seat. While the capillary passage 151 or 152 in a sense extends through the valve 126 for continuous catheter flushing at a seeping flow rate, it is also correct to consider the capillary passage 151 or 152 as bypassing the valve 126, as long as that valve is closed to its intended function, namely the fast flushing of the catheter system at the higher flow rate upon depression of the operator 128 within the protective shield 141.

A unique and highly beneficial feature of the second illustrated preferred embodiment or aspect of the subject invention is that the capillary passage 151 or 152 may be opened upon depression of the operator 128 from the rest position 31, whereby the opened capillary passage may be flushed at a rate higher than the seeping flow rate.

In this respect, the catheter flushing device 100, according to a second aspect of the invention, embodies methods and apparatus for flushing a catheter continually at a seeping flow rate through a capillary passage 151 or 152, and intermittently, upon opening of the valve 126, at a higher flushing flow rate. According to this second aspect of the subject invention, the capillary passage 151 or 152 is intermittently opened between continual flushings at the seeping flow rate, and such opened capillary passage is then flushed at the higher flushing flow rate.

In practice, the means at the capillary passage for intermittently opening such capillary passage 151 or 152 between continual flushings at the seeping flow rate may include the disclosed valve body 157 and valve seat 158, bounding the capillary passage 151 or 152 in their mutually engaged condition, and being separable from each other for opening the capillary passage 151 or 152 upon depression of the operator 128. The operator 128 and valve stem 127 connected to the capillary passage 151 may thus be viewed as a means at the capillary passage for intermittently opening such capillary passage between continual flushings at the seeping flow rate and/or as a means connected to the capillary passage for flushing the opened capillary passage at the higher flushing flow rate.

Figure 4:
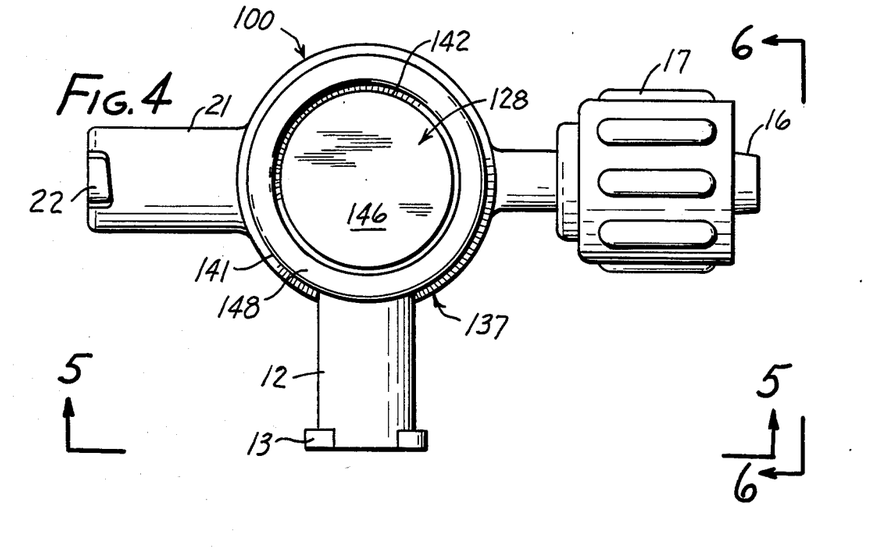
FIG. 4 is a top view of a catheter flushing device according to a further preferred embodiment of the subject invention.

In the embodiment illustrated in FIGS. 4 to 6, the catheter system and the opened capillary passage 151 or 152 are flushed simultaneously at the flushing flow rate.

By way of example, this is accomplished in the embodiment shown in FIGS. 4 to 6 by designing the flushing means to include the valve 126 having the valve seat 158 and valve body 157 seatable in such valve seat, and by extending the capillary passage between and along such valve body and valve seat. In this manner, the means for intermittently opening the capillary passage 151 or 152 may be provided by connecting means, such as the valve stem 127 and operator 128, to the valve body 157 for selectively separating such valve body from its valve seat 158.

In this manner, the embodiment shown in FIGS. 4 to 6 is realized, wherein the catheter system and the capillary passage 151 or 152 are simultaneously flushed at the higher flow rate upon a simple depression of the operator 128 by a human finger 29.

In this manner, the capillary passage 151 or 152 is recurringly opened and cleaned of any clogging contaminations in a convenient, reliable and automatic manner, assuring a maintenance of a predetermined continuous flushing at a predetermined low flow rate throughout active phases of operation of the catheter system.

To assure restoration of the capillary passage 151 or 152 after each separation and flushing thereof, the valve body 157 is preferably retained against rotation about its longitudinal axis, so that the corresponding adjacent portions of the valve body 157 and valve seat 158 bounding the capillary passage 151 or 152 remain always the same.

To this end a longitudinal keyway 171 may be provided in the valve stem 127 in parallel to its longitudinal axis. A corresponding key or pin 172 may be inserted into and through the housing 137 to project into the keyway 171, thereby preventing rotation of the valve body 157 relative to the valve seat 158.

The manually actuable operator 128, serving also for intermittently opening the capillary passage 151 or 152, is also protected by the shield 141 against accidental opening of the capillary passage 151 or 152. In this respect, reference should be had to the above description of the purpose and function of the raised protective shield 141 completely surrounding the operator 128 and surpassing such operator around its entire circumference, even in the operator rest position 31.

As disclosed in the above mentioned incorporated patents, all kind of monitoring equipment may be connected to the outlet passage 21 for monitoring the operating catheter system in any desired manner.

According to the detail shown in FIG. 7, an outlet passage 174 extends in the flushing device or apparatus from the valve 126 or capillary passage 151 to the infusion solution or flushing liquid outlet nipple 16 on the device or apparatus connectable or connected to the catheter 19. According to the embodiment of the invention illustrated with the aid of FIG. 7, a transducer 175 having a pressure-sensitive component 176 exposed to the inside of the outlet passage 174 between the capillary passage 151 and the outlet nipple 16 for sensing liquid pulsations in the outlet passage is provided thereat. As seen in FIG. 7, the pressure-sensitive component 176 is only near the liquid outlet 16 opposite the capillary passage 151. As also shown in FIG. 7, the outlet passage includes a concave cavity at 174 increasing in diameter from a bottom region, and the built-in transducer 175 has a pressure sensitive component 176 at that bottom region of that concave cavity for sensing liquid pulsations in that outlet passage. In the embodiment illustrated in FIG. 7, the concave cavity at 174 increases in diameter from its bottom region to a wider top opening facing the capillary passage 151. The capillary passage issues into the wider top of the concave cavity at 174, opposite the bottom at which the pressure sensitive component 176 of the built-in transducer 175 is located. The illustrated liquid outlet 16 issues from a side of the concave cavity at 174. In practice, the transducer 175, integral with the outlet passage 174, may be employed in various apparatus or devices for flushing a catheter continually at a seeping flow rate through a capillary passage and intermittently at a higher flushing flow rate.

By way of example, the built-in transducer 175 may include a transducer diaphragm or beam 177 mounted for deflection by pressure pulsations in the liquid passage 174. There may, for instance, be employed a transducer diaphragm or silicon beam 177 having one or more diffused gage elements 176 located thereon. The transducer 175 may have terminals 181 and 182 potted in potting compound deposits 183 and 184 which enclose also electric leads for the transducer elements and on which the transducer diaphragm or beam 177 may be mounted as well in the illustrated or any equivalent manner.

The transducer 175 may be connected to suitable monitoring equipment (not shown) for essentially any of the same purposes disclosed or mentioned in the incorporated patents. Because of the direct location and exposure of the transducer 175 at the path of the pulsating liquid, various highly precise measurement and monitoring functions regarding organisms connected to the catheter system via fluid in the catheter tubing 18 can be realized with the apparatus shown in FIG. 7 and equivalents thereof within the scope of the subject invention.

As a particularly advantageous feature in this connection, the embodiments shown in FIGS. 5 to 7 avoid the presence of any elastomeric or other pulse-dampening components in or at the fluid passage. In practice, this greatly enhances the attainable precision and quality of operation of the transducer 175 or of any pressure or similar transducer arrangement connected to the passage 21 in the embodiment shown in FIGS. 4 to 6, for instance.

To the same end, the elastomeric or flexible sleeve 35 or 135 is arranged within the shield structure 41 or 141, or its tapered portion 44 or 144, entirely outside any fluid passage in any catheter flushing device 10 and 100.

Figure 8:
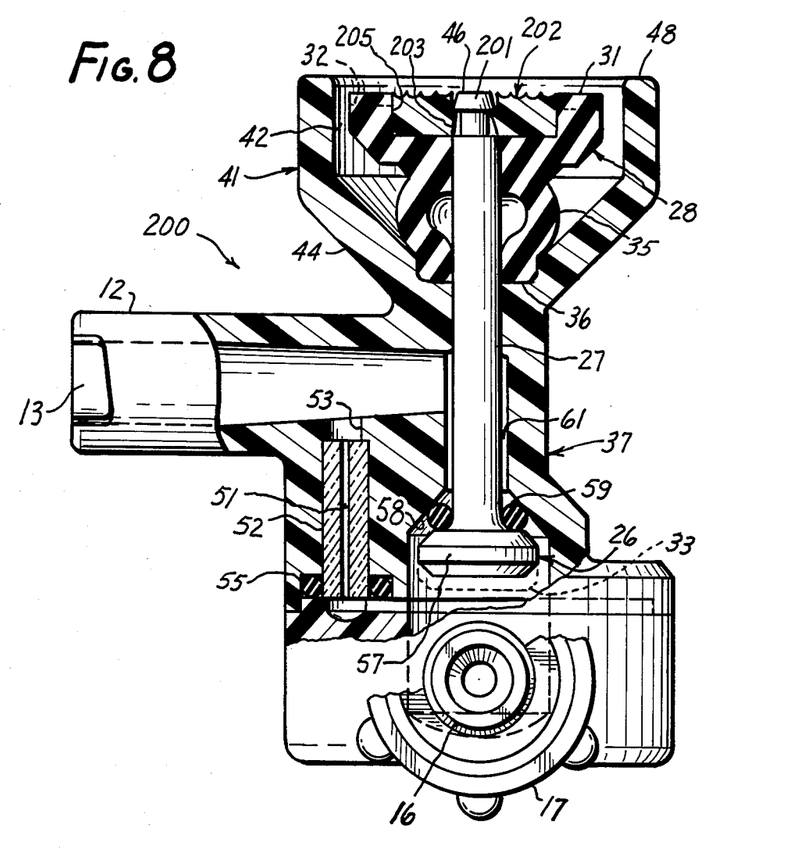
FIG. 8 is a view similar to FIG. 3, showing a modification of the catheter flushing device according to a preferred embodiment of the subject invention.

What has been said so far also applies to a large extent to the catheter flushing device 200 shown in FIG. 8. Accordingly, except for the parts shown in the exploded view of FIG. 9, the parts of the transducer shown in FIG. 8 and their operation and interrelationship may, by way of example, be assumed to be the same as those shown and disclosed in connection with FIGS. 1 to 3. Also, modifications disclosed with the aid of FIGS. 4 to 7, and including flushing capillary passages and built-in transducers, may be applied to the flushing device of FIG. 8 as desired or necessary for various applications.

Figure 9:
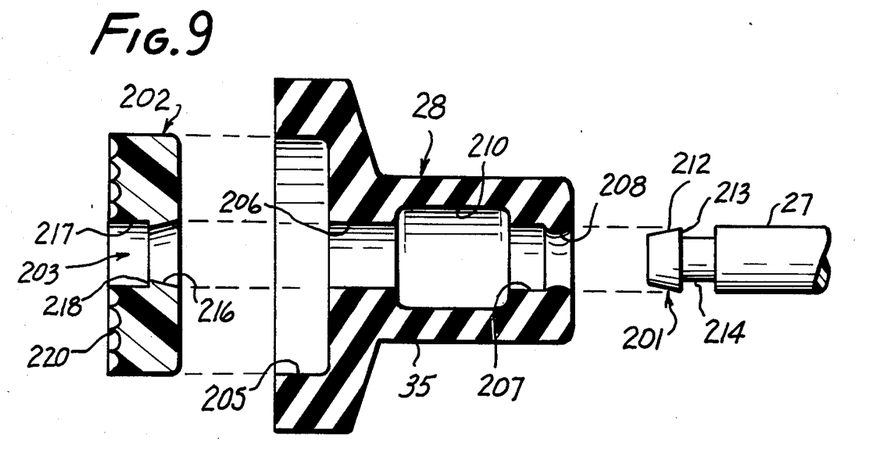
FIG. 9 is an exploded view of an assembly of parts used in the flushing device of FIG. 8.

According to FIGS. 8 and 9, a preferred embodiment of the subject invention provides the valve stem 27 with a snap-on connector end 201 at the operator 28. The preferred embodiment illustrated in FIGS. 8 and 9 also provides a retainer 202 for the operator and provides such retainer with a snap-on connection 203 for the connector 201. The preferred embodiment as seen in FIG. 8 retains the operator 28 at the valve stem 27 with the retainer 202 connected to the snap-on connector end 201 of the valve stem 27.

As seen in FIG. 8, the retainer 202 preferably is part of the operator 28. Referring to FIG. 3, showing a human finger in dotted outline at 29, it may be said that the retainer 202 preferably is a top part of the operator 28 engageable, or exposed to engagement, by such human finger.

Where the retainer 202 is part of the operator 28, the remainder of such operator preferably is made of an elastic material providing the above mentioned integral elastic sleeve 35 about the valve stem 27. Again, such integral elastic sleeve 35 may be employed for biasing the operator 28, including the retainer 202, to the above mentioned rest position, shown also in FIG. 8, before and after manual actuation of the valve 26 against the bias of the elastic sleeve 35 to the depressed position indicated at 32 and 33.

The retainer 202 preferably is a disc or similar object inlaid in the operator 28. To this end, the operator is provided with a circular, hollow-cylindrical or similar cavity 205 for receiving the retainer 202. The operator 28 also has bores or openings 206 and 207 for receiving the valve stem 27, as well as a circular lip 208 for engaging the valve stem in sealing contact. The operator 28 shown in FIG. 9 further has an enlarged-diameter hollow-cylindrical cavity 2iO between the openings 206 and 207 for providing the elastic sleeve 35.

The preferred snap-on connector 201 shown in FIGS. 8 and 9 has a tapered front end portion 212 at the free end of the valve stem 27, followed by a step 213 spaced from the remainder of the valve stem, or valve stem proper, by a reduced-diameter cylindrical portion 214.

The retainer 202 has a tapered first bore 216 at the snap-on connection 203 for receiving the tapered front end 212 of the connector 201. The tapered bore 216 is followed in the retainer 202 by an enlarged diameter opening 217, separated from the opening 216 by a step 218 corresponding to the step 213 of the connector 201.

During assembly of the flushing device 200, the valve stem 27 is inserted through the passage 61 into the cavity encompassed by the shield 41. The operator 28 shown in FIGS. 8 and 9 may be located in that cavity for reception of the valve stem top portion during insertion of such top portion in the cavity encompassed by the shield 41. Alternatively, the operator 28 may be inserted over the top end portion of the valve stem 27 while the same is projecting into the mentioned cavity.

In either case. the retainer 202 is snapped over the valve stem end portion 201. To this end, the tapered valve stem end 212 is moved relative to the correspondingly tapered retainer opening 216. In this respect, either the valve stem 27 or the retainer 202 may be maintained stationary, while the retainer 202 or valve stem 27 is moved relatively thereto. Alternatively, the valve stem 27 and retainer 202 may both be moved relatively into or over each other.

Upon continued relative movement of the valve stem end 201 into the retainer opening 203, or relative movement of the retainer 202 onto the valve stem end 201, the tapered front end 212 eventually enters the top retainer opening 217, whereby the reduced-diameter portion or step 218 of the retainer snaps under the step 213 of the connector above the reduced-diameter portion 214 which then is surrounded or encompassed by the tapered opening 216 of the retainer.

The completed assembly is seen in FIG. 8. The retainer 202 and, the valve stem end at 201, as desired, present a top operator surface 46 exposed for engagement, or engageable, by the above mentioned human finger 29, for an operation of the valve 26. As before, such top surface 46 preferably is again at all points and in all positions located inside the shield 41 below the rim 48, as a protection against accidental valve openings.

The retainer disc 202 preferably is of a more rigid material than the eleastic remainder or the sleeve 35 of the operator 28. In this manner, the retainer 202 avoids giving the person actuating the valve a certain spongy feeling conveyed by some rubbery or similar elastic materials. To the contrary, the retainer 202 provides a firm top surface at 46 which conveys to the person depressing the valve with his or her finger 29 a positive feeling of the desired valve actuation. To further increase the reliability of operation, the top surface 46 of the retainer 202 and, if desired, stem 27, may be provided with concentric circular grooves 220, or may otherwise be serrated.

At the same time, the retainer 202, at least at its snap-on connection 203, is sufficiently yielding for the desired reception of the snap-on valve stem connector end 201. There are many plastic or synthetic materials which satisfy the conditions or desiderata herein disclosed for the retainer 202. The valve stem advantageously may be made of the same material as the retainer 202.

In practice, the preferred embodiment shown in FIGS. 8 and 9 is characterized relative to the other illustrated embodiments by an easier and more reliable assembly which will withstand considerably more abuse by persons attempting to depress the operator unevenly or children attempting to squeeze or pull the operator out of the cavity surrounded by the protection shield 41.

A review of the illustrated preferred embodiments and their disclosure herein indicates that the subject invention and its various embodiments meet their initially stated objectives and avoid the disadvantages of prior or contemporary devices.

The subject invention and its embodiments are particularly useful in intravenous catheterization where a continuous infusion of a relatively small flow of liquid through the capillary passage 51, 151 or 152 prevents occlusion of the intravascular end of the catheter or in other parts of the system, thereby also permitting precise measurements of dynamic characteristics of the catheter transducer system. Against this background, the subject invention and its illustrated or otherwise disclosed embodiments provide improved means for effecting intermittent rapid flushing operations for clearing out the system of all air, for filling the system quickly with the requisite liquid and for otherwise checking or restoring the system from time to time for the benefit of the user and of the organism connected thereto.

The subject extensive disclosure will suggest or render apparent to those skilled in the art various modifications and variations within the spirit and scope of the invention and equivalents thereof.

I claim:

1. In a method of making a valve enabling flushing of a catheter intermittently at a flushing flow rate higher than a seeping flow rate, said valve being connectable between a supply of flushing liquid and the catheter and having a valve stem and a manually actuable valve operator on an end portion of the valve stem and engageable by a human finger for depression from a rest position, in which the valve is closed to flushing at the flushing flow rate, to a depressed position in which the valve is open for flushing of the catheter at the flushing flow rate, the improvement comprising in combination the steps of:

making said operator of an elastic material providing an integral elastic sleeve about said end portion of the valve stem:

employing said integral elastic sleeve for biasing said operator to said rest position before and after manual actuation against the bias of said elastic sleeve to said depressed position; and protecting said operator against accidental depression at all points thereof by completely surrounding said operator with a shield surpassing said operator around its entire circumference so as to require said human finger to penetrate into said shield for engagement of said operator prior to depression from said rest position against the bias of said elastic sleeve for an opening of said valve.

2. A method as claimed in claim 1, including the step of:

providing said operator with a top surface engageable by said human finger and being at all points and in all positions inside said shield.

3. A method as claimed in claim 1, including the step of:

providing said shield with an endless rim surpassing said operator at all points and in all positions thereof.

4. A method as claimed in claim 1, including the steps of:

providing a capillary passage bypassing said valve for flushing said catheter at said seeping flow rate.

5. A method as claimed in claim 4, including the steps of:

providing said capillary passage in said valve for an opening said capillary passage upon depression of said operator from said rest position and for flushing said opened capillary passage at a rate higher than said seeping flow rate.

6. A method as claimed in claim 4, including the steps of:

providing said valve and said capillary passage with an outlet nipple connectable to said catheter;

providing an outlet passage extending from said valve and said capillary passage to said outlet nipple connectable to the catheter; and locating at said outlet passage a transducer having a pressure sensitive component exposed to the inside of said outlet passage for sensing liquid pulsations in said outlet passage between said capillary passage and said nipple.

7. A method as claimed in claim 1, including the steps of:

providing said valve stem with a snap-on connector end at said operator;

providing said operator with a retainer and providing said retainer with a snap-on connection means for said connector end; and retaining said operator at said valve stem with said retainer connected via said snap-on connection means to said snap-on connector end.

8. In apparatus for flushing a catheter intermittently at a flushing flow rate higher than a seeping flow rate with the aid of a valve connectable between a supply of flushing liquid and the catheter and having a valve stem and a manually actuable valve operator on an end portion of the valve stem and engageable by a human finger for depression from a rest position, in which the valve is closed to flushing at the flushing flow rate, to a depressed position in which the valve is open for flushing of the catheter at the flushing flow rate, the improvement comprising in combination:

means for biasing said operator to said rest position before and after manual actuation, consisting of an elastic sleeve integral with said operator and extending about said end portion of the valve stem to a relatively stationary portion of said apparatus; and means for protecting said operator against accidental depression at all points thereof, including a shield surpassing said operator around its entire circumference so as to require said human finger to penetrate into said shield for engagement of said operator prior to depression from said rest position against the bias of said eleastic sleeve for and opening of said valve.

9. Apparatus as claimed in claim 8, including:

means for flushing said catheter at said seeping flow rate, including a capillary passage bypassing said valve.

10. Apparatus as claimed in claim 8, wherein:

said valve includes a valve body connected to said valve stem, and a valve seat for seating said valve body; and said apparatus includes means for flushing said catheter at said seeping flow rate when said valve body is seated in said valve seat, including a capillary passage extending between and along said valve body and valve seat.

11. Apparatus as claimed in claim 8, including:

a flushing liquid outlet nipple on said apparatus connectable to the catheter;

an outlet passage extending in said apparatus from said valve and said capillary passage to said outlet nipple; and means for sensing liquid pulsations in said outlet passage between said capillary passage and said nipple, including a transducer having a pressure sensitive component exposed to the inside of said outlet passage in said apparatus.

12. In apparatus for flushing a catheter continually at a seeping flow rate through a capillary passage and intermittently at a higher flushing flow rate, the improvement comprising in combination:

means at said capillary passage including a manually actuable operator for intermittently opening said capillary passage between continual flushings at said seeping flow rate;

means connected to said capillary passage for flushing said opened capillary passage at said higher flushing flow rate, said flushing means include a valve including a valve seat and a valve body seatable in said valve seat;

said capillary passage extends between and along said valve body and valve seat;

said means for intermittently opening said capillary passage includes means connected to said valve body for selectively separating said valve body from said valve seat; and said apparatus includes means for protecting said capillary passage against accidental opening, including a shield completely surrounding and surpassing said operator around its entire circumference.

13. Apparatus as claimed in claim 12, wherein:

said flushing means include means for flushing said catheter and said opened capillary passage simultaneously at said flushing flow rate.

14. In apparatus for flushing a catheter continually at a seeping flow rate through a capillary passage and intermittently at a higher flushing flow rate, the improvement comprising in combination:

means at said capillary passage including a manually actuable operator for intermittently opening said capillary passage between continual flushings at said seeping flow rate;

means connected to said capillary passage for flushing said opened capillary passage at said higher flushing flow rate, said flushing means include a valve including a valve seat and a valve body seatable in said valve seat;

said capillary passage includes a groove in a surface of one of said valve body and valve seat extending along and being laterally bounded by the other of said valve body and valve seat when said valve body is seated in said valve seat;

said means for intermittently opening said capillary passage include means connected to said valve body for selectively separating said valve body from said valve seat; and said apparatus includes means for protecting said capillary passage against accidental opening, including a shield completely surrounding and surpassing said operator around its entire circumference.

15. In apparatus for flushing a catheter continually at a seeping flow rate through a capillary passage and intermittently at a higher flushing flow rate, the improvement comprising in combination:

means at said capillary passage including a manually actuable operator for intermittently opening said capillary passage between continual flushings at said seeping flow rate;

means connected to said capillary passage for flushing said opened capillary passage at said higher flushing flow rate;

a flushing liquid outlet nipple on said apparatus connectable to the catheter;

an outlet passage extending in said apparatus from said capillary passage to said outlet nipple; and means for sensing liquid pulsations in said outlet passage between said capillary passage and said outlet nipple, including a built-in transducer integral with said outlet passage and having a pressure sensitive component exposed to the inside of said outlet passage in said apparatus.

16. In apparatus for flushing a catheter continually at a seeping flow rate through a capillary passage and intermittently at a higher flushing flow rate, the improvement comprising in combination:

a flushing liquid outlet on said apparatus connectable to the catheter;

an outlet passage extending in said apparatus from said capillary passage to said outlet; and means for sensing liquid pulsations in said outlet passage and said outlet, including a built-in transducer integral with said apparatus and having a pressure sensitive component in said apparatus only near said liquid outlet opposite said capillary passage, for sensing liquid pulsations in said outlet passage.

17. Apparatus as claimed in claim 16, wherein:

said pressure sensitive component includes a beam mounted for deflection by liquid pulsations in said outlet passage.

18. Apparatus as claimed in claim 16, wherein:

said pressure sensitive component includes a diaphragm mounted for deflection by liquid pulsations in said outlet passage.

19. Apparatus as claimed in claim 16, wherein:

said transducer has terminals and electric leads potted in said apparatus.

20. Apparatus as claimed in claim 16, wherein:

said outlet passage includes a concave cavity increasing in diameter from a bottom region; and said pressure sensitive component of the built-in transducer is at said bottom region of the concave cavity.

21. Apparatus as claimed in claim 20, wherein:

said liquid outlet issues from said concave cavity.

22. In a method of making a valve enabling flushing of a catheter intermittently at a flushing flow rate higher than a seeping flow rate, said valve being connectable between a supply of flushing liquid and the catheter and having a valve stem and a manually actuable valve operator on an end portion of the valve stem and engageable by a human finger for depression from a rest position, in which the valve is closed to flushing flow rate, to a depressed position in which the valve is open for flushing of the catheter at the flushing flow rate, the improvement of comprising in combination the steps of:

providing said valve stem with a snap-on connector end at said operator;

providing said operator with a retainer and providing said retainer with a snap-on connection means for retaining said operator at said valve stem via said snap-on connector end; and retaining said operator at said valve stem with said retainer connected via said snap-on connection means to said snap-on connector end.

23. A method as claimed in claim 22, wherein:

said retainer is inlaid in a remainder of said operator.

24. A method as claimed in claim 22, including the step of:

providing said retainer as a top part of said operator engageable by said human finger.

25. A method as claimed in claim 22, including the steps of:

providing said operator with an integral elastic sleeve about said end portion of the valve stem.

26. A method as claimed in claim 22, including the steps of:

providing said retainer as a top part of said operator engageable by said human finger;

making a remainder of said operator of an elastic material providing an integral elastic sleeve about said end portion of the valve stem; and employing said integral elastic sleeve for biasing said operator to said rest position before and after manual actuation against the bias of said elastic sleeve to said depressed position.

27. In apparatus for flushing a catheter intermittently at a flushing flow rate higher than a seeping flow rate with the aid of a valve connectable between a supply of flushing liquid and the catheter and having a valve stem and a manually actuable valve operator on an end portion of the valve stem and engageable by a human finger for depression from a rest position, in which the valve is closed to flushing at the flushing flow rate, to a depressed position in which the valve is open for flushing of the catheter at the flushing flow rate, the improvement comprising in combination:

means for biasing said operator to said rest position before and after manual actuation, including an elastic sleeve integral with said operator and extending about said end portion of the valve stem to a relatively stationary portion of said apparatus;

means for protecting said operator against accidental depression at all points thereof, including a shield surpassing said operator around its entire circumference so as to require said human finger to penetrate into said shield for engagement of said operator prior to depression from said rest position against the bias of said elastic sleeve for and opening of said valve; and a snap-on connector end on said valve stem;

said operator having a retainer connected to said valve stem via a snap-on connection means at said connector end.

28. In apparatus for flushing a catheter intermittently at a flushing flow rate higher than a seeping flow rate with the aid of a valve connectable between a supply of flushing liquid and the catheter and having a valve stem and a manually actuable valve operator on an end portion of the valve stem and engageable by a human finger for depression from a rest position, in which the valve is closed to flushing at the flushing flow rate, to a depressed position in which the valve is open for flushing of the catheter at the flushing flow rate, the improvement comprising in combination:

a snap-on connector end on said valve stem; and a retainer at a top of said operator exposed for engagement by said human finger and including a snap-on connection means for retaining said operator at said snap-on connector end.

29. Apparatus as claimed in claim 28, wherein:

said operator includes an elastic sleeve extending about said end portion of the valve stem to a relatively stationary portion of said apparatus.

30. Apparatus as claimed in claim 28, wherein:

said retainer is a disc inlaid in a remainder of said operator.

31. In apparatus for flushing a catheter continually at a seeping flow rate through a capillary passage and intermittently at a higher flushing flow rate, the improvement comprising in combination:

a flushing liquid outlet on said apparatus connectable to the catheter;

an outlet passage extending in said apparatus from said capillary passage to said outlet and including a concave cavity increasing in diameter from a bottom region to a wider top opening facing said capillary passage; and means for sensing liquid pulsations in said outlet passage and said outlet, including a built-in transducer integral with said apparatus and having a pressure sensitive component at said bottom region of said concave cavity, for sensing liquid pulsations in said outlet passage.

32. Apparatus as claimed in claim 31, wherein:

said liquid outlet issues from a side of said concave cavity.

33. Apparatus as claimed in claim 31, wherein:

said pressure sensitive component is located only near said liquid outlet opposite said capillary passage.

34. Apparatus as claimed in claim 23, wherein:

said liquid outlet issues from a side of said concave cavity.

* * * * *